US009213037B2

(12) United States Patent  
Kurono et al.

(10) Patent No.: US 9,213,037 B2  
(45) Date of Patent: Dec. 15, 2015

(54) SAMPLE ANALYZER AND SAMPLE ANALYZING METHOD

(71) Applicant: SYSMEX CORPORATION, Kobe-shi, Hyogo (JP)

(72) Inventors: Hiroshi Kurono, Kobe (JP); Yasuhiro Takeuchi, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 148 days.

(21) Appl. No.: 14/038,260

(22) Filed: Sep. 26, 2013

(65) Prior Publication Data

US 2014/0087472 A1   Mar. 27, 2014

(30) Foreign Application Priority Data

Sep. 27, 2012   (JP) .................................. 2012-214553

(51) Int. Cl.
*G01N 33/86* (2006.01)
*G01N 35/02* (2006.01)
*G01N 35/00* (2006.01)
*G01N 33/48* (2006.01)

(52) U.S. Cl.
CPC .......... *G01N 33/86* (2013.01); *G01N 35/00613* (2013.01); *G01N 35/00732* (2013.01); *G01N 33/48* (2013.01); *Y10T 436/113332* (2015.01)

(58) Field of Classification Search
CPC ....... G01N 33/48; G01N 33/86; G01N 35/00; G01N 35/00178; G01N 35/00613; G01N 35/00732; G01N 35/00891; G01N 35/02; G01N 35/00584; Y10T 436/11; Y10T 436/111666; Y10T 436/113332; Y10T 436/114165; Y10T 436/25375; Y10T 436/2575

USPC ............ 436/43, 45, 47, 48, 63, 69, 164, 174, 436/177, 180; 422/63, 65, 67, 68.1, 72, 73, 422/82.05, 82.09; 435/13
See application file for complete search history.

(56) References Cited

U.S. PATENT DOCUMENTS

| 2008/0050279 | A1* | 2/2008 | Fujita ............................... 422/67 |
| 2008/0183431 | A1* | 7/2008 | Matsuo et al. ................ 702/187 |
| 2009/0004681 | A1* | 1/2009 | Hoshiko et al. ................. 435/13 |
| 2010/0107744 | A1* | 5/2010 | Fukuda et al. ............... 73/64.56 |
| 2011/0123397 | A1* | 5/2011 | Yamato et al. .................. 422/63 |

FOREIGN PATENT DOCUMENTS

JP       2002-82118 A    3/2002

\* cited by examiner

*Primary Examiner* — Maureen Wallenhorst
(74) *Attorney, Agent, or Firm* — Sughrue Mion, PLLC

(57) ABSTRACT

Disclosed is a sample analyzer including a transporting part configured to transport a sample rack holding one or more samples, a measuring part configured to perform a measurement on the sample of the transported sample rack and a controller. The controller is programmed to perform an analysis of a predetermined item that requires at least first and second measurement results derived respectively from first and second samples obtained from the same subject and preprocessed in different ways, and if a measurement of the predetermined item is requested and a set of first and second samples obtained from the same subject and preprocessed in different ways are transported to the measuring part, the controller controls the measuring part to perform measurements on both of the first and second samples to derive the first and second measurement results and processes them to generate an analysis result of the predetermined item.

25 Claims, 14 Drawing Sheets

| Position | Sample No. | PPP | ADP | Epi | Col | Ris | Ara |
|---|---|---|---|---|---|---|---|
| 1, 2 | S10001 | ✓ | ✓ | | | | |
| 3, 4 | S10002 | ✓ | ✓ | ✓ | ✓ | ✓ | ✓ |
| 5, 6 | S10003 | ✓ | ✓ | ✓ | ✓ | | |
| 7, 8 | S10004 | ✓ | ✓ | | | | |
| 9, 10 | S10005 | ✓ | ✓ | | | | |

FIG.15

| | C21 | C22 | C23 | C24 | C25 | C26 | C27 | C28 | C29 |
|---|---|---|---|---|---|---|---|---|---|
| | Rack No. - position | Sample No. | PPP | ADP_s | ADP_e | ADP_min | ADP% | PT | APTT |
| L21 | 0005-01 | S10001 | 776 | | | | | | |
| L22 | 0005-02 | S10001 | | 1460 | 1412 | 1407 | | | |
| L23 | | S10001 | 776 | 1460 | 1412 | 1407 | 7.7 | | |
| L24 | 0007-04 | S10001 | | | | | | 11.3 | 23.5 |

D2

SAMPLE ANALYZER AND SAMPLE ANALYZING METHOD

FIELD OF THE INVENTION

The present invention relates to a sample analyzer and sample analyzing method for analyzing samples collected from subjects.

BACKGROUND

A known method for measuring platelet aggregation uses platelet rich plasma (PRP) samples derived from the plasma component containing a plenty of platelets obtained through weak centrifugation of whole blood collected from a patient, and platelet poor plasma (PPP) samples derived from the plasma component that does not substantially contain platelets obtained through strong centrifugation of whole blood. In this method, a reagent for causing platelet aggregation is added to the PRP sample and the respective light absorption of the PRP sample and the PPP sample is measured, then the platelet aggregation is calculated from the respective light absorptions.

Japanese Laid-Open Patent 2002-82118 discloses a complex measuring apparatus capable of performing platelet aggregation measurements, and measurements of biological components such as blood coagulation and fibrinolytic system substances through latex agglutination reaction. In this complex measuring apparatus, blood platelet aggregation is measured by adding reagent to the PRP sample, and separately loading the PPP sample and PRP sample in complex measuring apparatus.

The complex measuring apparatus disclosed in Japanese Laid-Open Patent 2002-82118 requires the addition of reagent to the PRP sample and loading of the PPP sample and PRP sample separately in the apparatus. The blood platelet aggregation must be calculated using both measurement results obtained by measuring the PRP sample and the PPP sample obtained by processing whole blood samples obtained from the same patient. Therefore, when measuring the PPP sample and PRP sample, it must be confirmed that the PPP sample and the PRP sample to be measured have been collected from the same patient (same whole blood sample). And if such confirmation is inadequate or erroneous confirmation is done, it may cause a mix-up of samples inadvertently.

SUMMARY OF THE PRESENT INVENTION

A first aspect of the present invention is a sample analyzer comprising: a transporting part configured to transport a sample rack holding one or more samples; a measuring part configured to perform a measurement on the sample of the transported sample rack; and a controller; wherein the controller is programmed to perform an analysis of a predetermined item that requires at least first and second measurement results derived respectively from first and second samples obtained from the same subject and preprocessed in different ways, if a measurement of the predetermined item is requested and a set of first and second samples obtained from the same subject and preprocessed in different ways are transported to the measuring part, the controller controls the measuring part to perform measurements on both of the first and second samples to derive the first and second measurement results and processes them to generate an analysis result of the predetermined item.

A second aspect of the present invention is a sample analyzer comprising: a transporting part configured to transport a sample rack holding one or more samples; a reading part configured to read identification information of the samples held in the sample rack; a measuring part configured to perform a measurement on the sample of the transported sample rack; and a controller programmed to: specify an analysis item requested with respect to a sample on a sample rack based on the identification information of the sample; designate another sample held in the same or different sample rack as a paired sample with the sample according to a predetermined rule when the specified analysis item is a predetermined analysis item using two samples which have undergone different preprocessing; cause the measuring part to perform measurements on the paired samples; and generate an analysis result of the predetermined item by processing the respective measurement results of the paired samples.

A third aspect of the present invention is a sample analyzing method comprising: transporting a sample rack holding a plurality of samples and includes a first sample and a second sample collected from the same subject and subjected to different preprocessing; identifying the first sample and the second sample from among the plurality of samples held in the sample rack; measuring the identified first sample and second sample; processing the respective obtained measurement results of the first sample and the second sample to obtain an analysis result for a predetermined item; and displaying the analysis result of the predetermined items.

BRIEF DESCRIPTION OF THE DRAWINGS

FIG. 15 shows an example of an measurement results screen.

EMBODIMENTS

The preferred embodiments of the present invention are described hereinafter with reference to the drawings.

[Structure of the Sample Analyzer]

Figure 1:
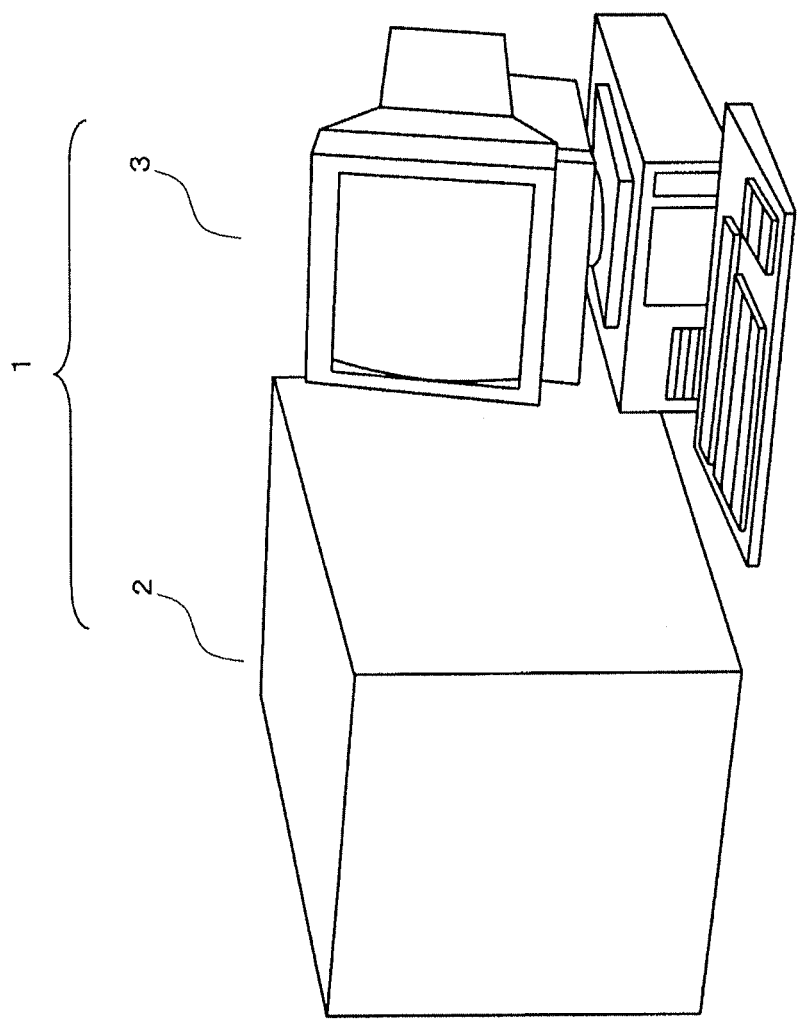
FIG. 1 shows the structure of an embodiment of the sample analyzer.
Figure 2:
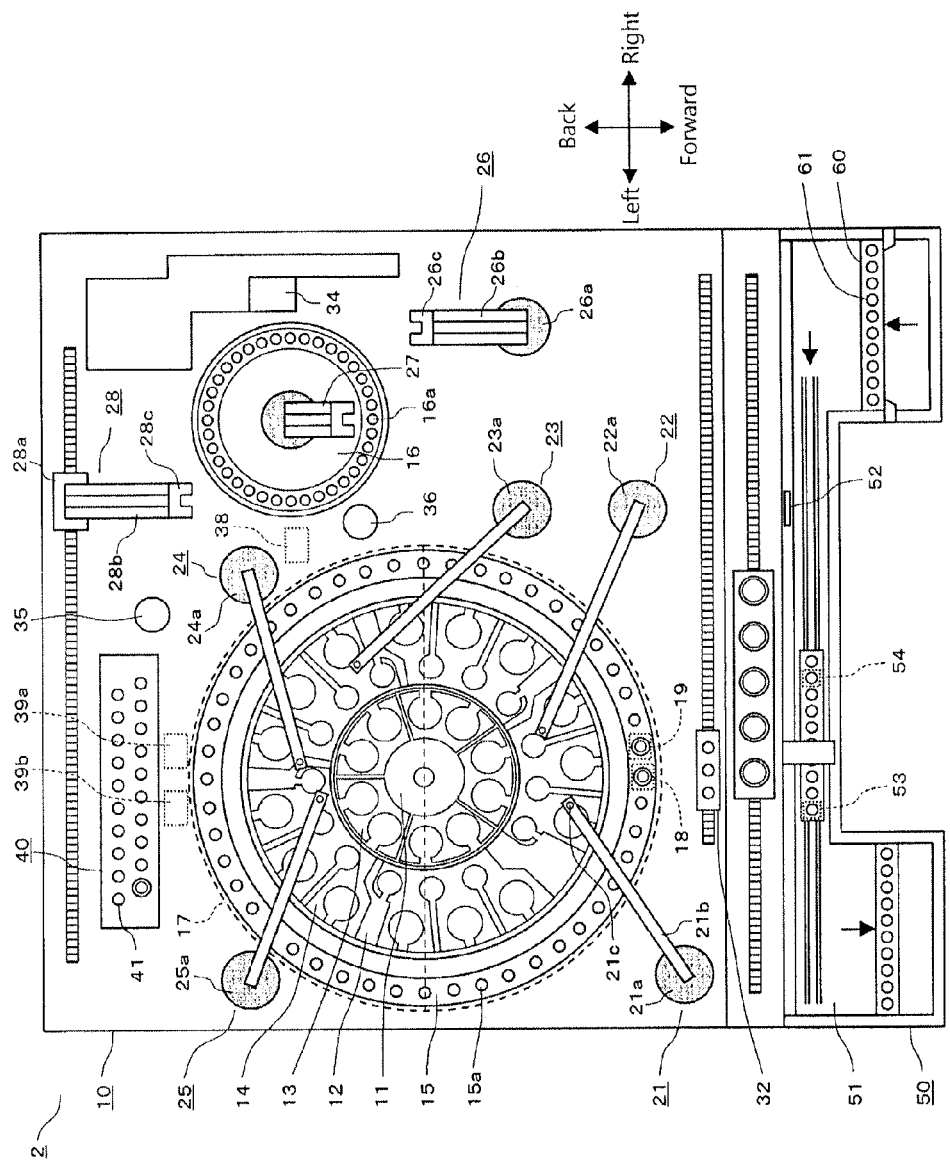
FIG. 2 is a plan view briefly showing the internal structure of the measuring device viewed from above.

FIG. 1 shows the structure of an embodiment of the sample analyzer 1. The sample analyzer 1 irradiates with light a measurement sample prepared by adding reagent to blood, and optically measures and analyzes the amount and degree of activity of a specific substance related to fibrinolytic function or blood clotting using a clotting method, synthetic substrate method, turbidimetric immunoassay, or agglutination method. The sample analyzer 1 is configured by a measuring device 2 for optically measuring a component contained in a sample, and an information processing device 3 for analyzing the measurement data obtained by the measuring device 2 and issuing operating instruction to the measuring device 2, FIG. 2 is a plan view briefly showing the internal structure of the measuring device 2 viewed from above. The measuring device 2 is configured by a measuring unit 10, detecting unit 40, and transporting unit 50.

The measuring unit 2 is configured by a first reagent table 11, second reagent table 12, first container rack 13, second container rack 14, cuvette table 15, heating table 16, table cover 17, first sample dispensing unit 21, second sample dispensing unit 22, first reagent dispensing unit 23, second reagent dispensing unit 24, third reagent dispensing unit 25, first catcher unit 26, second catcher unit 27, third catcher unit 28, cuvette transporter 32, cuvette port 34, and disposal ports 35 and 36.

The first reagent table 11, second reagent table 12, cuvette table 15, and heating table 16 are circular tables which are rotated independently in clockwise and counterclockwise directions. The rotational drive of these tables is accomplished by a step motor disposed below the tables at the back.

As shown in the drawing, five first container racks 13 and five second container racks 14 are detachably disposed on the top surfaces of the first reagent table 11 and the second reagent table 12. A holding part for holding the reagent container is formed on the first container rack 13 and the second container rack 14.

As shown in the drawing, a plurality of cuvette retaining holes 15a and 16a are respectively formed along the circumference of the cuvette table 15 and the heating table 16. When cuvettes are set in the cuvette retaining holes 15a and 16a, the circumferential position of the cuvettes move coincident with the rotation of the cuvette table 15 and heating table 16. The heating table 16 heats the cuvettes set in the retaining holes 16a to a predetermined temperature.

The table cover 17 is disposed so as to cover the top surface of the first reagent table 11, second reagent table 12, and cuvette table 15. The table cover 17 also has a folding mechanism in the center part to allow opening only the front half. A plurality of holes (not shown) are provided in the table cover 17. Dispensing by the first sample dispensing unit 21, second sample dispensing unit 22, first reagent dispensing unit 23, second reagent dispensing unit 24, and third reagent dispensing unit 25 is accomplished through the plurality of holes.

As shown in the drawing, the first sample dispensing unit 21 has a support part 21a, arm 21b, and dispensing part 21c. The support part 26a is driven in rotation by a step motor disposed below the bottom surface at the back. The support part 21a supports the arm 21b, and the arm 21b is driven in vertical directions by a step motor. The dispensing part 21c is mounted on the tip of the arm 21b and has a pipette. Sample is aspirated and ejected using the pipette.

When the support part 21a is rotated, the dispensing part 21c is moved on the circumference pivoting on the support part 21a. When at the sample aspirating position, the dispensing part 21c aspirates the sample directly below the position, and when at the sample discharging position, the dispensing part 21c discharges the sample into a cuvette directly below the position. Note that the second sample dispensing unit 22, first reagent dispensing unit 23, and second reagent dispensing unit 24 have the same structure as the first sample dispensing unit 21. That is, the second sample dispensing unit 22 has a support part 22a, and the support part 22a is driven in rotation by a step motor disposed behind the bottom surface. The first reagent dispensing unit 23, second reagent dispensing unit 24, and third reagent dispensing unit 25 are respectively provided with a support part 23a, 24a, and 25a, and the support parts 23a, 24a, and 25a are driven in rotation by step motors disposed behind the bottom surface.

As shown in the drawing, the first catcher unit 26 is configured by a support part 26a for supporting an arm 26b, an extendable arm 16b, and a gripping part 26c. The support part 26a is driven in rotation by a step motor disposed below the bottom surface at the back. The gripping part 26c is mounted on the tip of the arm 26b, and is capable of gripping the cuvette. Note that the second catcher unit 27 has the same structure as the first catcher unit 26 and is rotated by a step motor.

As shown in the drawing, the third catcher unit 28 has a support part 28a for supporting the arm 28b, an extendable arm 28b, and a gripping part 28c mounted on the tip of the arm 28b. The support part 28a is drivable along a rail arranged in a lateral direction. The grip 28c is capable of holding a cuvette.

The cuvette transporter 32 is driven on a rail in a lateral direction. The cuvette transporter 32 is provided with a hole for holding a cuvette.

Normally, a new cuvette is supplied to the cuvette aperture 34. New cuvettes are set in the hole for retaining the cuvette of the cuvette transporter 32 and the cuvette retainer hole 15a of the cuvette table 15 by the first catcher unit 26 and the second catcher unit 27. The disposal apertures 35 and 36 are holes for disposing of the cuvette which is no longer needed after analysis is completed.

The top surface of the detection unit 40 is provided with ten retaining holes 41 for accommodating cuvettes, and detector having a light emitting part and a light receiving part is disposed on the bottom surface in the unit. The light emitting part irradiates light toward the cuvette held in the retaining hole 41. The light receiving part is disposed on the opposite side of the cuvette from the light emitting part and receives the light transmitted through the cuvette and outputs an electrical signal corresponding to the amount of received light. Hence, when a cuvette is set in the retaining hole 41, the detector detects the characteristic information of light absorption of the contents of the cuvette.

One of the retaining holes 41 of the detection unit 40 is provided with a magnet disposed near the hole. A motor 411 (not shown in the drawing) is connected to the magnet so that the magnet can be rotated by the motor. When a cuvette containing a liquid and a stirrer bar is set in the retaining hole 41 with the magnet, the magnet is rotated by the drive of the motor so that the stirrer bar in the cuvette is rotated in conjunction with the rotation of the magnet and the liquid is mixed thereby.

The transporting unit 50 has a transport path 51 and a barcode reader 52. The bottom surface of the transport path 51 has a squared U-shape with a right tank region on the right side, a connection region in the center, and a left tank region on the left side. The sample barcode reader 52 reads the barcode on the barcode label adhered to the sample container 61 held in the sample rack 60 transported in the connection region.

The sequence of operation while performing sample analysis is described below.

The sample rack 60 holding a plurality of sample containers 61 is set in the right tank region of the transport path 51. The sample rack 60 is moved backward in the right tank region, then is moved leftward to the connection region. At this time the barcode label adhered to the sample containers 61 are read by the sample barcode reader 52. Then, the sample rack 60 is positioned at a predetermined location in the connection region. When the sample aspiration is completed in the connection region, the sample rack 60 is moved leftward in the connection region, then moved forward in the left tank region.

The first sample dispensing unit 21 aspirates the sample from the sample container 61 which is disposed at a predetermined sample aspirating position 53 of the connection region of the transport path 51. The sample aspirated by the first sample dispensing unit 21 is then discharged into a cuvette set in a cuvette retaining hole 15*a* positioned at the front sample discharging position 18 of the cuvette table 15.

The second sample dispensing unit 22 aspirates the sample in a cuvette disposed at the sample aspirating position 19, or the sample in the sample container 61 disposed at a predetermined sample aspirating position 54 of the connection region of the transport path 51. The sample aspirated by the second sample dispensing unit 22 is discharged into the cuvette placed in the cuvette transporter 32.

When the sample is discharged to the cuvette, the cuvette transporter 32 is driven rightward on the rail with a predetermined timing. Then, the cuvette containing the sample placed in the cuvette transporter 32 by the first catcher unit 26 is placed in the cuvette retaining hole 16*a* of the heating table 16.

The second catcher unit 27 then grips the cuvette containing the sample placed in the retaining hole 16*a*, and moves the cuvette to the reagent discharge position 38. The first reagent dispensing unit 23 aspirates reagent (primary reagent) from a predetermined reagent container disposed on the first reagent table 11 or the second reagent table 12, and discharges the aspirated reagent at the reagent discharge position 38. Hence, when the reagent is discharged, the second catcher unit 27 mixes the contents of the cuvette and again sets the cuvette in the cuvette retaining hole 16*a* of the heating table 16.

In this case the cuvette held in the cuvette retaining hole 16*a* on the heating table 16 is gripped by the third catcher unit 28 and positioned at the reagent discharging position 39*a* or 39*b*. The second reagent dispensing unit 24 and the third reagent dispensing unit 25 aspirate reagent (secondary reagent) from a predetermined reagent container disposed on the first reagent table 11 or the second reagent table 12, and respectively discharge the aspirated reagent into cuvette at the reagent discharge position 39*a* and 39*b*. After the reagent has been discharged as described above, the third catcher unit 28 sets the cuvette containing the discharged reagent in the retaining hole 41 of the detection unit 40. Thereafter, in the detection unit 40, the optical characteristic information is detected from the measurement sample in the cuvette.

Note that although both mixing of the reagent (primary reagent) by the first reagent dispensing unit 23 and mixing of the reagent (secondary reagent) by the second reagent dispensing unit 24 and third reagent dispensing unit 25 are performed in this case, the mixing of the primary reagent may not be performed depending on the content of the analysis. In that case, the step of mixing the primary reagent is skipped and detection of the optical characteristic information is performed after the mixing of the secondary reagent.

The cuvette, which is unnecessary after optical measurements have been completed by the detection unit 40, is gripped by the third catcher unit 28 and is moved to directly above the disposal aperture 35 where it is released for disposal to the disposal aperture 35. The cuvette held in the cuvette retaining hole 15*a* of the cuvette table 15 is unneeded after the analysis is completed, and is positioned near the second catcher unit 27 by rotating the cuvette table 15. The second catcher unit 27 grips the unneeded cuvette held in the cuvette retaining hole 15*a* and discards the cuvette in the disposal aperture 36.

Figure 3:
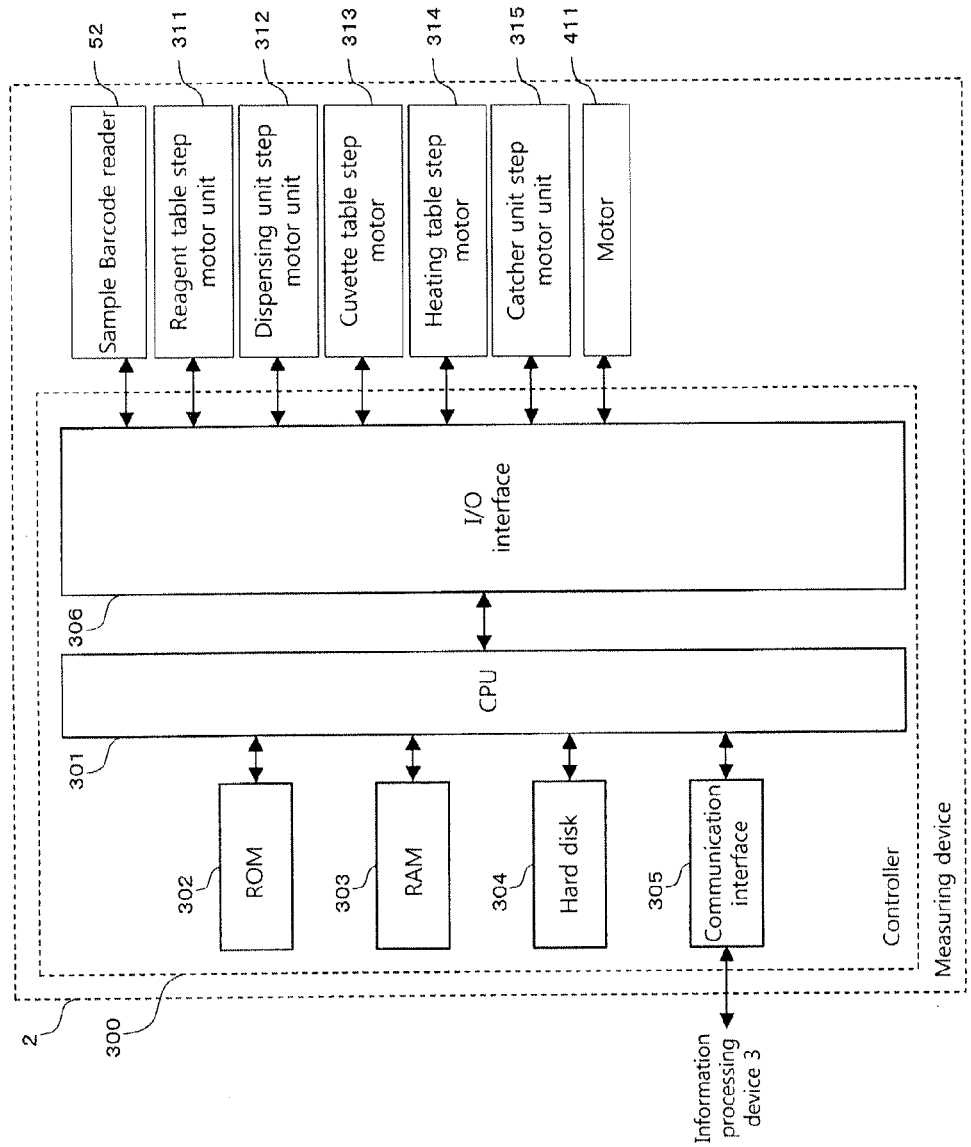
FIG. 3 shows the circuit structure of the measuring device.

FIG. 3 shows the circuit structure of the measuring device 2.

The measuring device 2 has a controller 300, sample barcode reader 52, reagent table step motor unit 311, dispensing unit step motor unit 312, cuvette table step motor 313, heating table step motor 314, catcher unit step motor unit 315, and stirrer drive motor 411. The controller 300 has CPU 301, ROM 302, RAM 303, hard disk 304, communication interface 305, and I/O interface 306.

The CPU 301 is capable of executing a computer program stored in the ROM 302 and a computer program loaded in the RAM 303. The RAM 303 is used when reading the computer programs stored in the ROM 302 and recorded on the hard disk 304. The RAM 303 is also used as the work area of the CPU 301 when the CPU 301 executes the computer programs. The hard disk 304 holds various installed computer programs that are executed by the CPU 301, including an operating system and application programs, as well as the data used when executing these computer programs. Data communication with the information processing device 3 is also accomplished through the communication interface 305.

The CPU 301 controls the sample barcode reader 52, reagent table step motor 311, dispensing unit step motor 312, and motor 411 through the I/O interface.

The reagent table step motor unit 311 is configured by a step motor for rotating the first reagent table 11, and step motor for rotating the second reagent table 12 independently from the first reagent table 11. The dispensing unit step motor unit 312 is configured by five step motors for independently rotating the support part 21*a* of the first sample dispensing unit 21, support part 22*a* of the second sample dispensing unit 22, support part 23*a* of the first reagent dispensing unit 23, support part 24*a* of the second reagent dispensing unit 24, and support part 25*a* of the third reagent dispensing unit 25. The catcher unit step motor unit 315 is configured by a step motor to rotate the support part 26*a* of the first catcher unit 26, and a step motor to rotate the second catcher unit 27.

Figure 4:
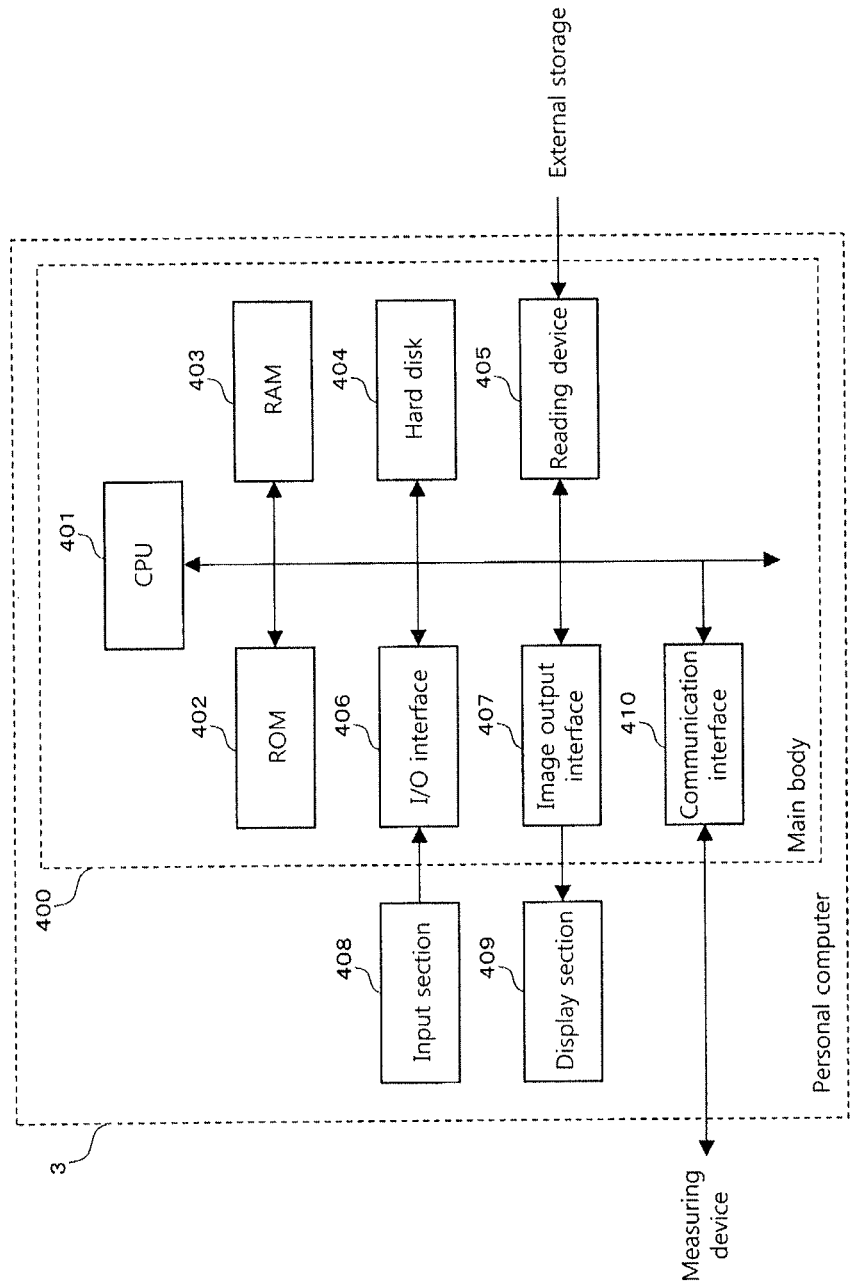
FIG. 4 shows the circuit structure of the information processing device.

FIG. 4 shows the circuit structure of the information processing device 3.

The information processing unit 3 is configured by a personal computer having a main body 400, input section 408, and display 409. The main body 400 has a CPU 401 ROM 402, RAM 403, hard disk 404, reading device 405, I/O interface 406, image output interface 407, and communication interface 410.

The CPU 401 is capable of executing a computer program stored in the ROM 402 and a computer program loaded in the RAM 403. The RAM 403 is used when reading the computer program stored in the ROM 402 and recorded on the hard disk 404. The RAM 403 is also used as the work area of the CPU 401 when the CPU 401 executes the computer programs The hard disk 404 holds various installed computer programs that are executed by the CPU 401, including an operating system and application programs, as well as the data used when executing these computer programs. That is, computer programs used to control the measuring device 2 and control the execution of the sample measuring operation are installed on the hard disk 404.

The reading device 405 is a CD drive or DVD drive capable of reading computer programs and data recorded on a recording medium. The I/O interface 406 is connected to the input section 408 configured by a mouse and keyboard, and the user uses the input section 408 to input data to the information processing unit 3. The image output interface 407 is connected to the display section 409 configured by a display of some type, and the image output interface 407 outputs image signals corresponding to the image data to the display 409. The display 409 displays images based on the input image signals. Data communication with the information processing device 3 is also accomplished through the communication interface 410.

[Operation of the Sample Analyzer]

The operation of the sample analyzer 1 of the present embodiment is described below. The sample analyzer 1 of the present embodiment is capable of measuring samples for measurement items related to blood coagulation and fibrinolytic function (hereinafter referred to as "blood coagulation items"), and measurement items related to platelet aggregation (hereinafter referred to as "platelet aggregation items").

Figure 5:
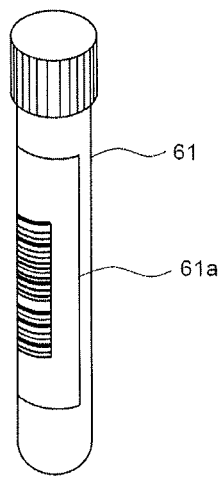
FIG. 5 is a perspective view showing the exterior structure of the first-type sample container.

The present embodiment uses two types of sample containers, a first-type sample container and a second-type sample container. FIG. 5 is a perspective view showing the exterior structure of the first-type sample container. The first-type sample container 61 is a blood collection tube having a long cylindrical body. A cap is provided at the top end of the sample container 61, and this cap seals the first-type sample container 61. Adhered to the first-type sample container 61 is a barcode label 61a on which is printed a barcode representing a sample number to identify the sample contained therein. The cap on the top end is removed when the measurement is performed.

Figure 6:
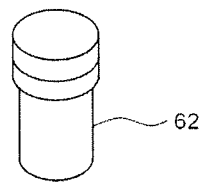
FIG. 6 is a perspective view showing the exterior structure of the second-type sample container.

FIG. 6 is a perspective view showing the exterior structure of the second-type sample container 62. The second-type sample container 62 is short and cup-like compared to the first-type sample container 61. A cap is provided at the top end of the second-type sample container 62, and this cap seals the second-type sample container 62. A barcode label is not adhered to the second-type sample container 62.

The first-type sample container 61 is used for both of the measurements of blood coagulation items and platelet aggregation items, and the second-type sample container 62 is used only for the measurement of platelet aggregation. The whole blood sample collected from a patient requiring measurement of blood coagulation is subjected to weak centrifugation processing, and the plasma or serum is accommodated in the first-type sample container 61. The plasma or serum is used for measurements of blood coagulation items. The whole blood sample collected from a patient requiring measurement of platelet aggregation items is first subjected to weak centrifugation processing, and the obtained supernatant is accommodated in the second-type sample container 62 as a PRP sample. The remainder of the sample left after the PRP sample has been collected is subjected to strong centrifugation processing, and the obtained supernatant is accommodated in the first-type sample container 61 as a PPP sample. The PRP sample contains the plasma component that includes a plenty of platelets, whereas the PPP sample contains the plasma component that contains very few platelets. The PRP sample and the PPP sample are used to measure platelet aggregation items.

Figures 7, 8:
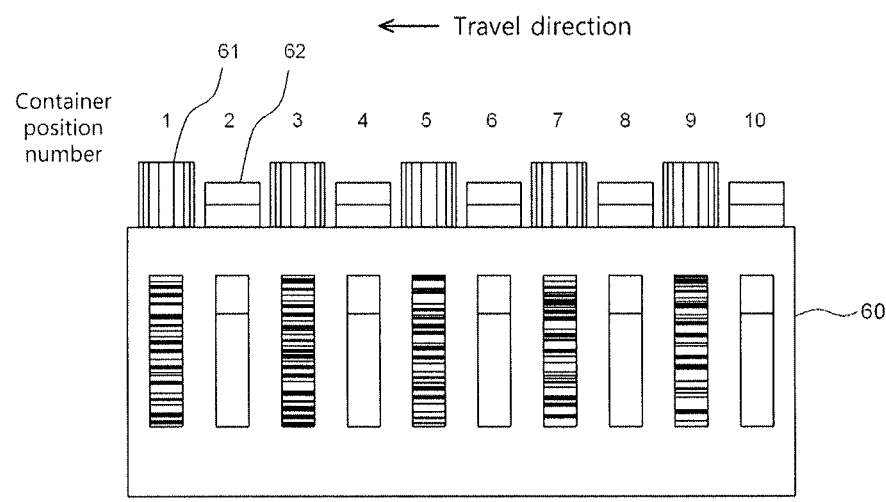
FIG. 7 is a front view of the sample rack holding the first-type sample container and the second-type sample container.
FIG. 8 shows an example of the measurement order recording screen.

The first-type sample container 61 and the second-type sample container 62 containing the samples described above are held in a sample rack and supplied to the sample analyzer 1. FIG. 7 is a front view of the sample rack holding the first-type sample container 61 and the second-type sample container 62. The sample rack 60 is capable of holding ten sample containers aligned in a row. That is, the sample rack 60 has ten container holding positions, and each holding position is capable of holding a first-type sample container 61 or a second-type sample container 62.

In the case where a measurement of the blood coagulation items is performed, only the first type of sample containers 61 containing plasma or serum are held on the sample rack 60. In the case where a measurement of the platelet aggregation items is performed, only the first type of sample container 61 containing the PPP sample and the second type of sample container 62 containing the PRP sample are held on the sample rack 60. That is, the first-type sample container 61 containing plasma or serum used for blood coagulation measurement items will not be held in one sample rack 60 together with the first-type sample container 61 containing PPP sample or the second-type sample container 62 containing PRP sample. FIG. 7 shows a sample rack 60 used for measurement of platelet aggregation items. The first-type sample container 61 containing PPP sample and a second-type sample container 62 containing PRP sample are alternately disposed in the sample rack 60 supplied for measurement of platelet aggregation items. That is, the first-type sample containers 61 containing PPP sample are placed at odd numbered holding positions on the sample rack 60, and the second-type sample containers 62 containing PPP sample are placed at even numbered holding positions on the sample rack 60. The numbers of the holding positions are assigned sequentially 1 through 10 from the holding position on the downstream side in the travel direction of the sample rack 60. The pair of two adjacent PPP sample and PRP sample were collected from the same patient. For example, the PPP sample at holding position 1 and the PRP sample at holding position 2 were collected from the same patient.

A single sample number is assigned to the paired set of PPP sample and PRP sample collected from the same patient. Since PPP sample and the PRP are held adjacent to one another in the sample rack 60, the sample number is acquired from the barcode label 61a of the first-type sample container 61 containing the PPP sample and this sample number is also applied to the PRP sample. That is, the paired set of PPP sample and PRP sample can be specified according to the rule that the paired set of PPP sample and PRP sample are disposed adjacent to one another in holding positions of the sample rack 60. Therefore, when the sample number is acquired from the barcode label of the first-type sample container 61 containing the PPP sample among the paired set of PPP sample and PRP sample, this sample number is specified as the sample number of the corresponding PRP sample even though a sample number label such as a barcode label is not adhered to the second-type sample container 62.

The user can record the sample measurement order in the sample analyzer 1. FIG. 8 shows an example of the measurement order recording screen. FIG. 8 shows an example of a screen for recording a measurement order of platelet aggregation items. The user can see the order recording screen D1 on the display section 409 by using the input section 408 of the information processing device 3. The sample measurement order can be recorded in unit of sample rack in the order recording screen D1. The order recording screen D1 has a table format which includes a column C1 representing the holding positions of the sample rack 60, column C2 for inputting the sample number, column C3 for inputting the measurement order for measurement item "PPP," column C4 for inputting the measurement order for measurement item "ADP (adenosine diphosphate)," column C5 for inputting measurement order for measurement item "Epi (epinephrine)," column C6 for inputting measurement order for measurement item "Col (collagen)," column C7 for inputting measurement order for measurement item "Ris (ristocetin)," and column C8 for inputting measurement order for measurement item "Ara (Arachidonic acid)." In the order recording screen D1 for recording measurement orders for platelet aggregation items, each of lines are assigned for each pair of holding positions holding the PPP sample and PRP sample which are assigned the same sample number, and measurement order can be recorded for each line individually. In the example of FIG. 8, the set of holding positions 1 and 2 are provided one line, and sample number "S10001" is entered in this line. The measurement order for measurement items "PPP" and "ADP" are provided in this line. The recorded measurement order is stored in the hard disk 404 of the information processing device 3. Note that when the order recording screen D1 is displayed, the measurement orders are entered by default in column C3 (order for PPP) and column C4 (order for ADP).

When the measurement order has been recorded as described above, the user sets the first-type sample container 61 or the second-type sample container 62 in the sample rack 60, and places the sample rack 60 in the transport unit 50 of the sample analyzer 1. Thereafter, the sample analyzer 1 begins sample analysis.

Figure 9:
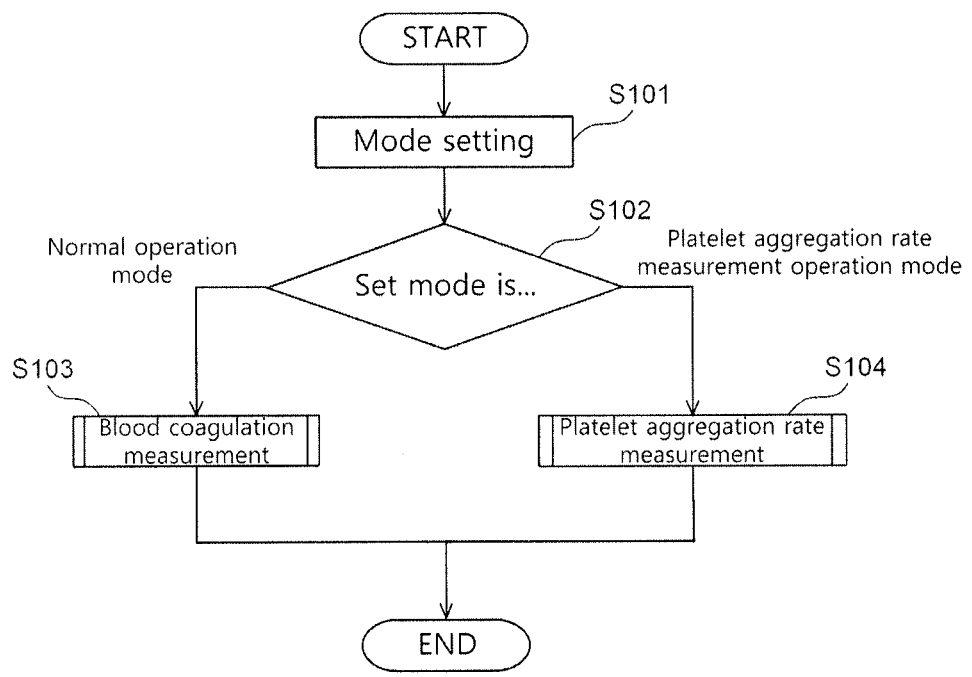
FIG. 9 is a flow chart showing the sequence of the operation performed by the sample analyzer of the embodiment.

FIG. 9 is a flow chart showing the protocol of the operation of an embodiment of the sample analyzer 1. The operating mode can be set in the sample analyzer 1; the user can designate either a normal measurement mode to perform sample measurements of measurement items other than platelet aggregation items (blood coagulation items), or a platelet aggregation rate measurement mode to perform sample measurements of platelet aggregation items. The CPU 401 of the sample analyzer 1 first sets the operation mode of the sample analyzer 1 (step S101). In this process, the operation mode instruction from the user is accepted and the operation mode of the sample analyzer 1 is set according to the instruction of the user. When an operation mode instruction is not received from the user, the default value of the normal measurement mode is set. The setting information of the operation mode is then stored on the hard disk 404.

The CPU 401 then determines whether the set operating mode is the normal measurement mode or the platelet aggregation rate measurement mode (step S102). When the set operating mode is the normal measurement mode (step S102: "normal measurement mode"), the CPU 401 controls the measuring device 2 to perform the blood coagulation measurement operation in the sample analyzer 1 (step S103). When the set operating mode is the platelet aggregation rate measurement mode (step S102: "platelet aggregation rate measurement mode"), the CPU 401 controls the measuring device 2 to perform the platelet aggregation rate measurement operation in the sample analyzer 1 (step S104). After the blood coagulation measurement operation or the platelet aggregation rate measurement operation is completed, the CPU 401 ends the process.

Figure 10:
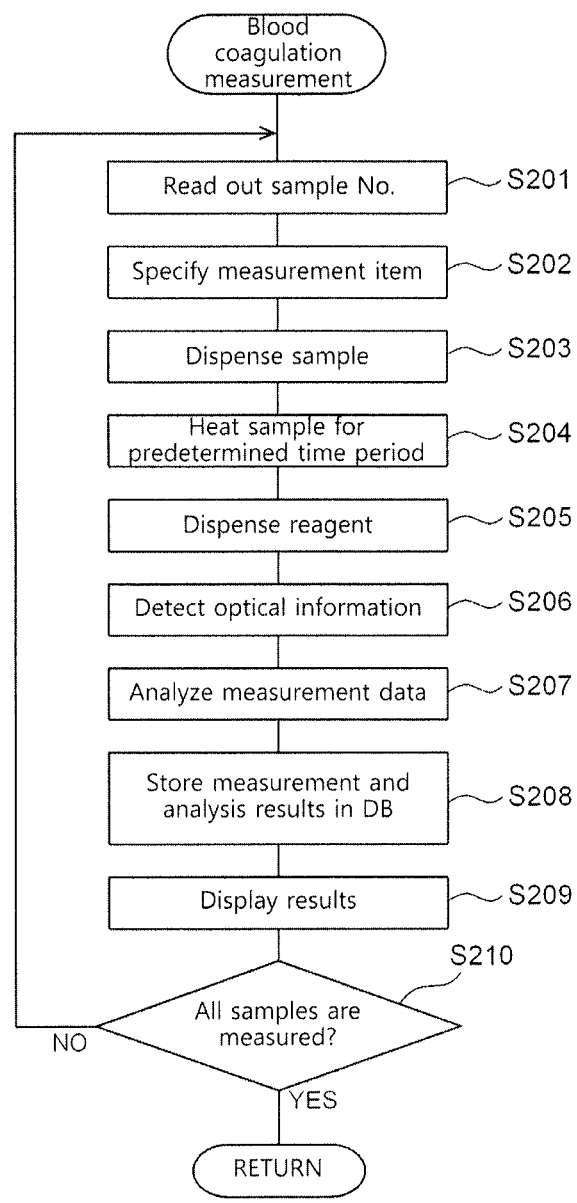
FIG. 10 is a flow chart showing the protocol of the blood coagulation measurement operation.

FIG. 10 is a flow chart showing the protocol of the blood coagulation measurement operation. Note that the operation when measuring a sample for the measurement item "PT (prothrombin time)" is described below. When performing the blood coagulation measurement operation, the sample rack 60 (that is, the sample rack 60 holding only the first-type sample container 61 containing plasma or serum for the blood coagulation measurement) to be used in the blood coagulation item measurement is placed in the right tank region of the transport path 51 of the transporting unit 50. The sample rack 60 is moved backward in the right tank region, then is moved leftward to the connection region. At this time the barcode label adhered to the sample container 61 is read by the sample barcode reader 52 (step S201).

The CPU 401 specifies the measurement order stored in the hard disk 404 corresponding to the read sample number, and specifies the measurement items ordered by the measurement order (step S202).

The CPU 401 then transmits the data instructing the measurement of the sample to the controller 300 of the measuring device 2 based on the specified measurement items. The CPU 301 performs controls to position the sample rack 60 at a predetermined location in the connection region. The first sample dispensing unit 21 or the second sample dispensing unit 22 then aspirates the sample in the sample container 61 and discharges the aspirated sample into a cuvette placed in the cuvette transporter 32 (step S203).

The CPU 301 then controls the first catcher unit 26 to grip the cuvette containing the sample disposed in the cuvette transporter 32 and place the gripped cuvette in the cuvette retaining hole 16a of the heating table 16. The sample is therefore heated for a predetermined time, e.g., 3 minutes (step S204).

When the sample heating time has elapsed, the CPU 301 controls the third catcher unit 28 to grip the cuvette held in the cuvette retaining hole 16a of the heating table 16, and position the cuvette at the reagent discharge position 39a or 39b. The CPU 301 controls the second reagent dispensing unit 24 or the third reagent dispensing unit 25 to aspirate reagent from a reagent container at a predetermined location on the first reagent table 11 or the second reagent table 12, and discharge the aspirated reagent into the cuvette at the reagent discharge position 39a or 39b (step S205). When the reagent is discharged as described above, the CPU 301 controls the third catcher unit 28 to set the cuvette containing the discharged reagent in the retaining hole 41 of the detection unit 40. Thereafter, the optical characteristic information of the degree of light absorption is detected from the measurement sample in the cuvette via the detection unit 40 (step S206).

The measurement data including the obtained light absorption information are transmitted to the information processing device 3. The CPU 401 of the information processing device 3 analyzes the measurement data and generates measurement results (step S207). The CPU 401 stores the measurement results in a measurement result database provided on the hard disk 404 (step S208), and makes the display section 409 to display the measurement results (step S209).

The CPU 401 determines whether an unmeasured sample remains in the sample rack 60 (step S210). If an unmeasured sample remains in the sample rack 60 (step S210: NO), the process returns to step S201 and the subsequent processes of steps following step S201 are performed for the next sample. When all samples of the sample rack 60 have been measured (step S210: YES), the CPU 401 returns the process to the call address of the blood coagulation measurement operation in the main routine.

When the aspiration is completed for all samples in the sample rack 60 in the connection region, the sample rack 60 is moved leftward in the connection region, then moved forward in the left tank region.

Although the operation of measuring a sample is described in terms of the blood coagulation item "PT" in the above description of the blood coagulation measurement operation, the sample analyzer 1 is capable of measuring sample for other blood coagulation items such as, for example, PTT (partial prothrombin time), APTT (active partial thromboplastin time), Fbg (fibrinogen concentration), LA (lupus anticoagulant), AT-III, D-dimer, FDP. When measuring a sample for blood coagulation items other than "PT," the measurement is performed according to the measurement protocol corresponding to that item.

Figure 11:
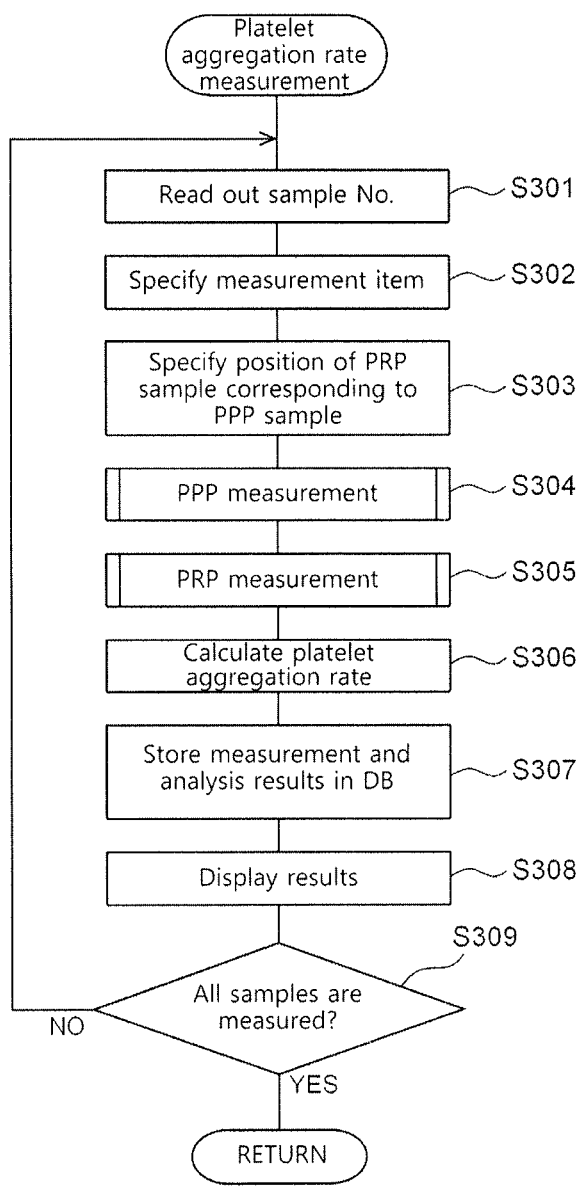
FIG. 11 is a flow chart showing the protocol of the blood platelet aggregation measurement operation.

FIG. 11 is a flow chart showing the protocol of the platelet aggregation rate measurement operation. When performing the platelet aggregation rate measurement operation, the sample rack 60 used for measurement of platelet aggregation items (that is, the sample rack 60 holding only the first-type sample container 61 containing PPP sample and the second-type sample container 62 containing the PRP sample) placed in the right tank region of the transport path 51 of the transporting unit 50. The sample rack 60 is moved backward in the right tank region, then is moved leftward to the connection region. The barcode label adhered to the first-type sample container 61 containing the PPP sample is read at this time by the barcode reader 52 (step S301).

The CPU 401 specifies the measurement order corresponding to the read sample number stored in the hard disk 404, and specifies the measurement items to be measured based on the measurement order (step S302). When the measurement item is specified, the CPU 401 specifies the holding position in the sample rack 60 of the PRP sample paired with the PPP sample from which the sample number was read, according to the rule of arrangement of samples with respect to the holding positions (step S303). For example, when the PPP sample from which the sample number was read is held in the holding position 1 of the sample rack 60, the position of the PRP sample corresponding to the PPP sample is specified as the holding position 2.

The CPU 401 then transmits data instructing the measurement of the PPP sample to the controller 300 of the measuring device 2. Hence, the PPP sample measurement operation is performed by the sample analyzer 1 (step S304).

Figure 12:
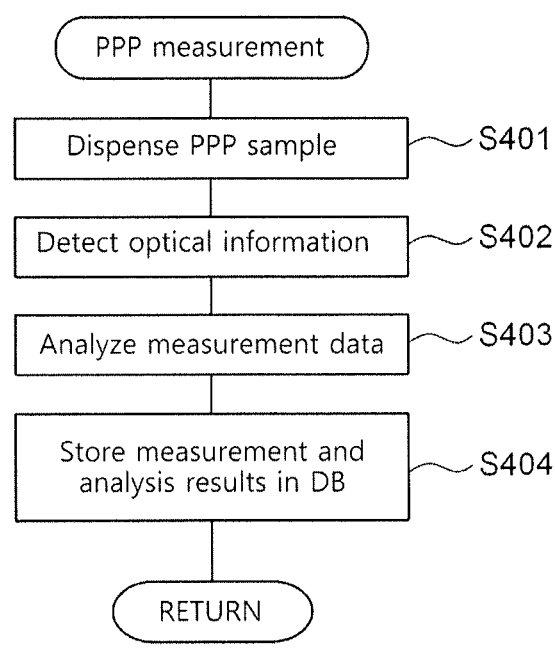
FIG. 12 is a flow chart showing the protocol of the PPP sample measurement operation.

FIG. 12 is a flow chart showing the protocol of the PPP sample measurement operation. During the PPP sample measurement operation, the CPU 301 performs controls to position the sample rack 60 at a predetermined location in the connection region. The first sample dispensing unit 21 or the second sample dispensing unit 22 then aspirates the PPP sample in the first sample container and discharges the aspirated sample into a cuvette placed in the cuvette transporter 32 (step S401).

The CPU 301 then controls the first catcher unit 26 and the third catcher unit 28 to place the cuvette containing the dispensed PPP sample in the retaining hole 41 of the detection unit 40. Thereafter, the optical characteristic information of the degree of light absorption is detected from the PPP sample in the cuvette via the detection unit 40 (step S402).

Figure 14A:
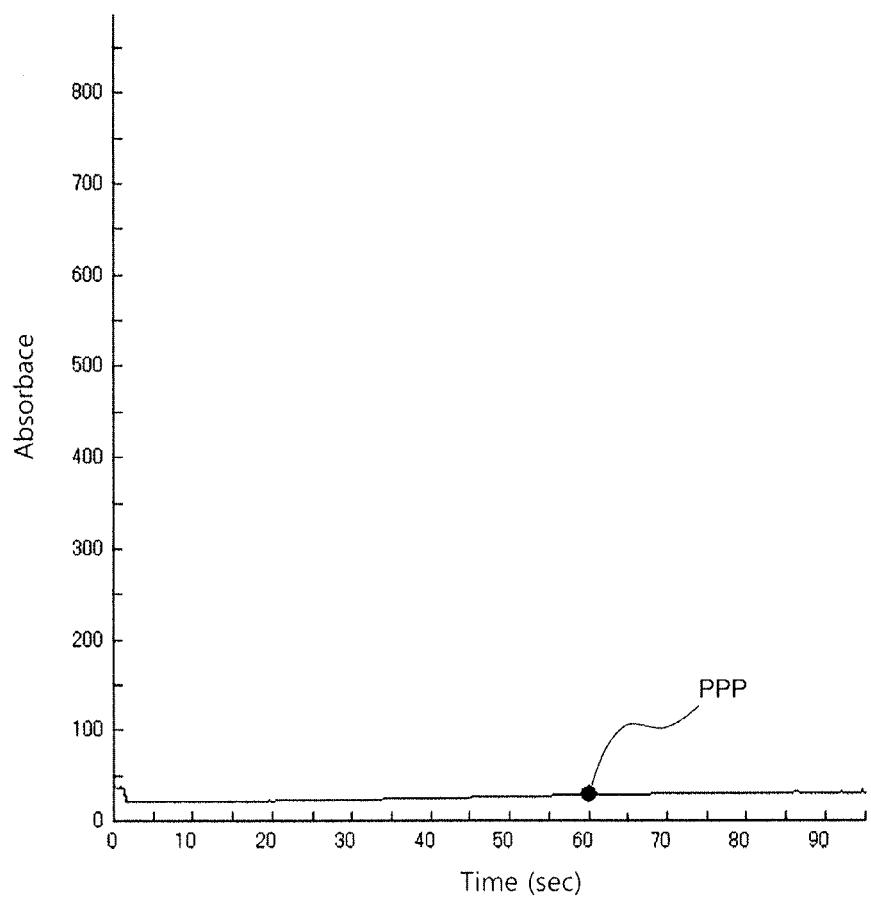
FIG. 14A is a graph showing an example of the measurement data of the PPP sample.

The measurement data of the PPP sample including the obtained light absorption information are transmitted to the information processing device 3. The CPU 401 of the information processing device 3 analyzes the measurement data and generates measurement results of the PPP sample (step S403). Analysis of the measurement data of the PPP sample is described below. FIG. 14A is a graph showing an example of the measurement data of the PPP sample. In FIG. 14A, the vertical axis represents the light absorption and the horizontal axis represents the time. In the process performed in step S402, the light absorption of the PPP sample is detected continuously over a predetermined time. The measurement data are therefore time series light absorption data. In the process performed in step S403, the light absorption at a predetermined moment (for example, 60 seconds after the start of the measurement) is designated the measurement result from among the time series light absorption data.

When obtaining the measurement results of the PPP sample, the CPU 401 stores the measurement results of the "PPP" measurement item in the measurement result database on the hard disk 404 (step S403), and returns the process to the call address of the PPP sample measurement operation in the platelet aggregation rate measurement operation.

The CPU 401 then transmits the data instructing the measurement of the PRP sample to the controller 300 of the measuring device 2 based on the specified measurement items (for example, "ADP"). Hence, the PRP sample measurement operation is performed by the sample analyzer 1 (step S305).

Figure 13:
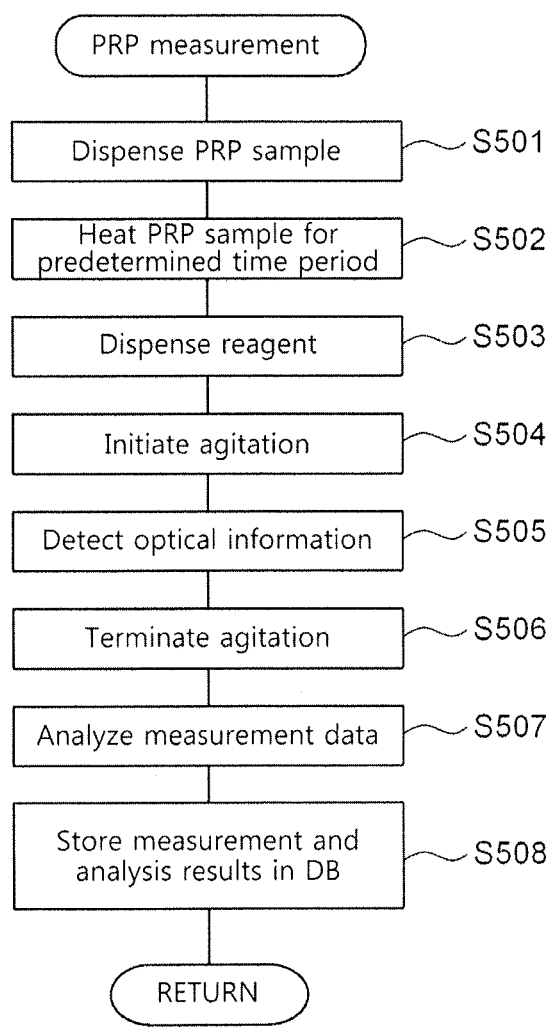
FIG. 13 is a flow chart showing the protocol of the PRP sample measurement operation.

FIG. 13 is a flow chart showing the protocol of the PRP sample measurement operation. When the PRP sample measurement starts, a cuvette with an inserted stirrer bar is placed on the cuvette table 15. During the PRP sample measurement operation, the CPU 301 performs controls to position the sample rack 60 at a predetermined location in the connection region. The first sample dispensing unit 21 or the second sample dispensing unit 22 aspirates from the second-type sample container containing the PRP sample disposed adjacent to the PPP sample that was measured in the PPP sample measurement operation, and discharges the aspirated sample into the cuvette with the inserted stirrer bar placed on the cuvette table 15 (step S501).

The CPU 301 then controls the first catcher unit 26 to grip the cuvette containing the sample disposed in the cuvette table 15 and place the gripped cuvette in the cuvette retaining hole 16a of the heating table 16. The sample is therefore heated for a predetermined time, e.g. 3 minutes (step S502).

When the sample heating time has elapsed, the CPU 301 controls the third catcher unit 28 to grip the cuvette held in the cuvette retaining hole 16a of the heating table 16, and position the cuvette at the reagent discharge position 39a or 39b. The CPU 301 controls the second reagent dispensing unit 24 or the third reagent dispensing unit 25 to aspirate reagent (platelet aggregation inducing agent) from a reagent container at a predetermined location on the first reagent table 11 or the second reagent table 12, and discharge the aspirated reagent into the cuvette at the reagent discharge position 39a or 39b (step S503). When the reagent is discharged as described above, the CPU 301 controls the third catcher unit 28 to set the cuvette containing the discharged reagent in the retaining hole 41, which is provided with a stirrer bar rotating magnet, of the detection unit 40. Thereafter, the CPU 301 controls the motor 411 to rotate the magnet at the retaining hole 41 of the detecting unit 40, hence, rotating the stirrer bar in the cuvette to start agitating the measurement sample in the cuvette (step S504).

The optical characteristic of light absorption is detected from the measurement sample in the cuvette in the detecting unit 40 while the stirrer bar is rotated (step S505). When the light absorption detection is completed, the CPU 301 stops the motor 411, which ends the agitation of the measurement sample in the cuvette (step S506).

Figure 14B:
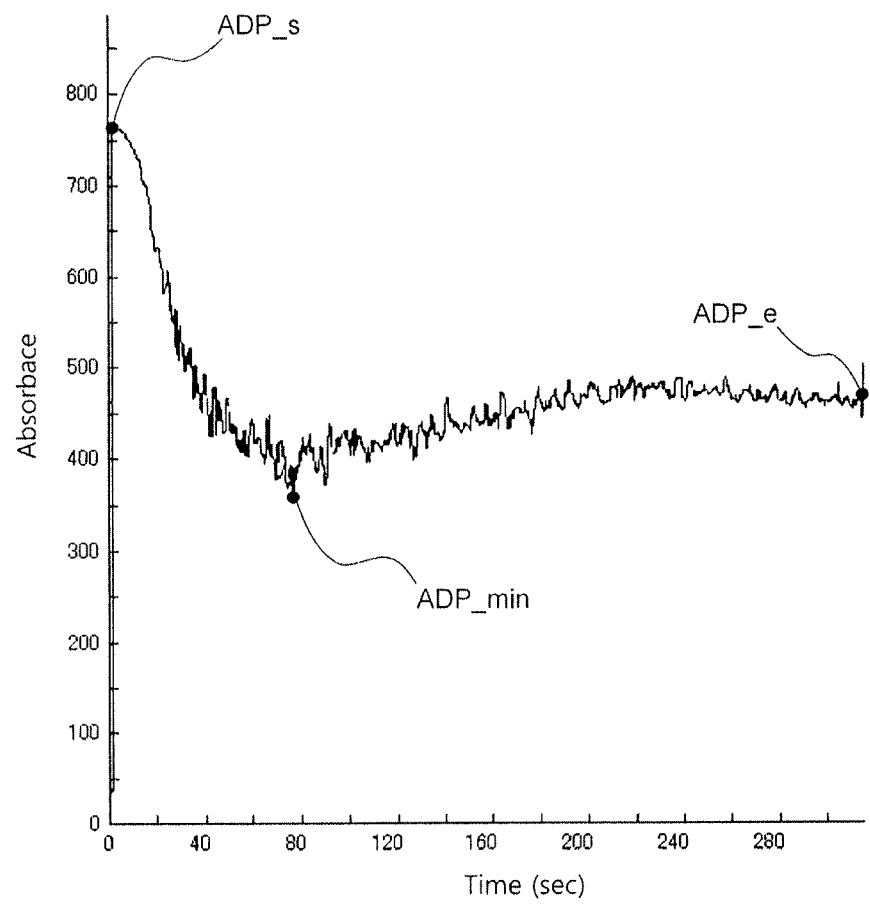
FIG. 14B is a graph showing an example of the measurement data of the PRP sample.

The measurement data of the PRP sample including the obtained light absorption information are transmitted to the information processing device 3. The CPU 401 of the information processing device 3 analyzes the measurement data and generates measurement results of the PRP sample (step S507). Analysis of the measurement data of the PRP sample is described below. FIG. 14B is a graph showing an example of the measurement data of the PRP sample. In FIG. 14B, the vertical axis represents the light absorption and the horizontal axis represents the time. The measurement of the PRP sample for platelet aggregation item "ADP" is described below. In the process performed in step S505, the light absorption of the PRP sample is detected continuously over a predetermined time. The measurement data are therefore time series light absorption data. In the process of step S507, the light absorption ADP_s at the start of measurement, light absorption ADP_e at the end of measurement, and light absorption minimum value ADP_min are extracted from the time series light absorption data as the measurement results. Note that although the measurement results when ADP is the measurement item is described above, other platelet aggregation items such as light absorption at the start of measurement, light absorption at the end of measurement, and light absorption minimum value may similarly be extracted from the measurement data as the measurement results.

When obtaining the measurement results of the PRP sample, the CPU 401 stores the measurement results of the PRP sample in the measurement result database on the hard disk 404 (step S508), and returns the process to the call address of the PRP sample measurement operation in the platelet aggregation rate measurement operation.

When the PPP sample measurement operation and the PRP sample measurement operation are completed, the CPU 401 calculates the platelet aggregation rate based on the PPP sample measurement result and the PRP sample measurement result (step S306). This process is described below. The operational expression of the platelet aggregation rate is stored on the hard disk 404. For example, Equations (1) and (2) below may be stored on the hard disk 404.

$$ADP\%=((ADP\_s-ADP\_min)/(ADP\_s-PPP))\times 100 \quad (1)$$

$$Epi\_e\%=((Epi\_s-Epi\_e)/(Epi\_s-PPP))\times 100 \quad (2)$$

Since the measurement item described in this embodiment is ADP, the CPU 401 substitutes the PPP sample measurement result and the PRP sample measurement result "ADP_s" and "ADP_min" in equation (1) to calculate the platelet aggregation rate "ADP %". Thus, the platelet aggregation rate "ADP %" is obtained for the patient from whom the mutually corresponding PPP sample and the PRP sample were collected.

For example, if the measurement item is Epi, the Epi reagent is used to measure the PRP sample instead of the ADP reagent, and the measurement results of the PPP sample and the measurement result of the PRP sample "Epi_s" and "Epi_e" are substituted in equation (2) to obtain the platelet aggregation rate "Epi_e %".

The CPU 401 stores the platelet aggregation rate measurement results obtained above in the measurement result database provided on the hard disk 404 (step S307), and displays the measurement result on the display section 409 (step S308).

FIG. 15 shows an example of a measurement results screen. FIG. 15 shows an example of measurement results when samples collected from the same patient are measured for blood coagulation item "PT" and "APTT" and platelet aggregation item "ADP". The measurement result screen D2 is a display type screen having a column C21 representing the rack number and holding positions of the sample rack 60, column C22 representing the sample number, column C23 representing the measurement result for measurement item "PPP," column C24 representing the measurement result for measurement item "ADP_s", column C25 representing measurement results for measurement item "ADP_e", column C26 representing measurement results for measurement item "ADP_min" column C27 representing measurement results for measurement item "ADP %", column C28 representing measurement results for measurement item "PT", and column C29 representing measurement results for measurement item "APTT". The sample rack number is allocated to sample racks to identify the sample rack. The example shown in FIG. 15 shows the PPP sample of sample number "S10001" held at holding position 1 of the sample rack having the sample rack number "0005", and the PRP sample of sample number "S10001" held at holding position 2 of the sample rack, and the measurement results of the measured PPP sample and the PRP sample measured for "ADP" are also shown. In the example of FIG. 15, the plasma sample of sample number "S10001" is held at holding position 4 of the sample rack having the sample rack number "0007", and the measurement results are shown when the plasma sample is measured for measurement items "PT" and "APTT".

A line is provided for each sample container in the measurement result screen. A separate line is provided for the sample containers in relation to the calculation results of the platelet aggregation items. Line L21 in FIG. 15 corresponds to the first-type sample container 61 containing the PPP sample, and the PPP measurement results are represented. Line L22 corresponds to the second-type sample container 62 containing the PRP sample, and the measurement results "ADP_s", "ADP_e" and "ADP_min" are represented. In line L21, the measurement results of the PPP sample indicate the measurement item "PPP" as the measurement value, and in line L22 the measurement results of the PRP sample indicate the measurement items "ADP_s", "ADP_e" and "ADP_min" as the measurement values. That is, the measurement results of "PPP", "ADP_s", "ADP_e", and "ADP_min" parameters used to calculate the platelet aggregation rate are displayed as independent results of the measurement items of the platelet aggregation rate. Hence, the user obtains the data "PPP", "ADP_s", "ADP_min" used to calculate the platelet aggregation rate measurement results from the screen D1 as the measurement results of the respective measurement items, and uses these data as clinical data.

Line L23 in FIG. 15 corresponds to the calculation result of platelet aggregation items, and shows the calculated platelet aggregation rate "ADP %". The measurement values of "PPP", "ADP_s", "ADP_e", and "ADP_min" are also shown in line L23 as the parameters used to calculate "ADP %". Line L24 corresponds to the first-type sample container 61 containing plasma sample for the blood coagulation item, and shows the measurement results of the blood coagulation items "PT", and "APTT".

If the measurement results of the blood coagulation items and the measurement results of the platelet aggregation items of the same patient are recorded in the measurement results database, the measurement results of the blood coagulation items and the measurement results of the platelet aggregation items can be displayed in a single screen D2. Since the user can confirm the measurement results of the blood coagulation items and the measurement results of the platelet aggregation items of the same patient in a single screen D2, the effort of confirming measurement results by the user can be saved because separate screens are not required to verify the particular measurement results of the blood coagulation items and the measurement results of the platelet aggregation items via data useful for diagnosis by physicians and the like. Measurement results of platelet aggregation rate and parameters used to calculate the platelet aggregation rate also are shown in the same screen D2. Since the user can confirm the measurement results of the platelet aggregation items and the parameters used to calculate the platelet aggregation rate on the same screen D2, the user need not search for parameter data in the measurement results database when the user needs the parameters used for the calculation in addition to the platelet aggregation rate, hence reducing the labor on the user.

The CPU 401 then determines whether an unmeasured sample remains in the sample rack 60 (step S309), if an unmeasured sample remains in the sample rack 60 (step S309: NO), the process returns to step S301 and the subsequent processes of steps following step S301 are performed for the next sample. When all samples of the sample rack 60 have been measured (step S309: YES), the CPU 401 returns the process to the call address of the platelet aggregation rate measurement operation in the main routine.

Other Embodiments

Note that although the above embodiment is described in terms of specifying mutually corresponding PPP sample and PRP sample using the rule such that PPP sample and PRP sample collected from the same patient are held in adjacent holding positions in the sample rack 60, the present invention is not limited to this configuration. Insofar as the holding positions for holding the mutually corresponding PPP sample and PRP sample are predetermined in the rule, the mutually corresponding PPP sample and PRP sample can be defined according to the rule. For example, if it is ruled so that holding positions 1 through 5 of the sample rack 60 may be used for the PPP sample and holding position 6 through 10 of the sample rack 60 may be used for the PRP sample, the controller may be programmed to recognize that the pair of samples held at the holding positions 1 and 6 are the pair of the PPP sample and the PRP sample that are mutually corresponding to and the pair of samples held at the holding positions 2 and 7 are the pair of the PPP sample and the PRP sample that are mutually corresponding to. By defining one holding position and other holding position for holding the pair of sample containers in the arrangement rule of sample container on a sample rack in advance, according to the rule, the mutually corresponding sample containers can be specified.

It may be ruled to arrange the mutually corresponding PPP sample and PRP sample at adjacent position regardless the distance between them. That is, in this case the holding position of the PPP sample and the holding position of the PRP sample need not be adjacent unless another sample is not placed between the PPP sample and the PRP sample. For example, if the PPP sample is held at the holding position 1 of the sample rack 60 and the corresponding PRP sample is held at holding position 5 of the sample rack 60 with no other sample held at holding positions 2 through 4, the PPP sample at holding position 1 and the PRP sample at holding position 5 can be specified as the pair of PPP and PRP samples having been collected from the same patient by this rule.

The arrangement rule of the mutually corresponding PPP sample and PRP sample is not limited to arrange these samples on same sample rack. It be may ruled that the mutually corresponding PPP sample and PRP sample are respectively placed on predetermined holding positions of different two sample racks. For example, the arrangement rule may made so that only the PPP samples shall be held in one sample rack and only the PRP samples shall be held in another sample rack, and the mutually corresponding PPP sample and PRP sample shall be held at the same holding position in the respective sample racks. According to this arrangement rule, if a PPP sample is held at holding position 1 of one sample rack 60 and the PRP sample which has been collected from the same patient as the PPP sample is held at the holding position 1 of the other sample rack 60, the PPP sample and the PRP sample can be specified as mutually corresponding.

Although the above embodiment is described in terms of the user manually setting the operating mode, the present invention is not limited to this configuration. When a barcode label on which is printed the rack number is adhered to the sample rack beforehand, the rack number can be read by a barcode reader and the rack number can be used to determine whether the sample rack is used for blood coagulation measurements or platelet aggregation measurements; the CPU 401 can then automatically set the operating mode to the normal measurement mode when the sample rack is used for blood coagulation measurements, or the CPU 401 can automatically set the operating mode to the platelet aggregation rate measurement mode when the sample rack is used for platelet aggregation measurements.

Although the above embodiment is described in terms of the user manually setting the operating mode, the present invention is not limited to this configuration. When a sample number is read from a barcode label 61a adhered to the first-type sample container 61 by a barcode reader, the sample number can be used to determine whether the sample is used for blood coagulation measurements or platelet aggregation measurements; the CPU 401 can then automatically set the operating mode to the normal measurement mode when the sample is used for blood coagulation measurements, or the CPU 401 can automatically set the operating mode to the platelet aggregation rate measurement mode when the sample is used for platelet aggregation measurements.

Although the above embodiment is described in terms of reading a sample number when a barcode reader reads a barcode printed on a barcode label 61a which is adhered to a first-type sample container 61, the present invention is not limited to this configuration. For example, a wireless tag containing the recorded sample number also may be affixed to the first-type sample container 61, and the sample number can be read from the wireless tag by a wireless communication unit provided in the sample analyzer.

Although the above embodiment is described in terms of adhering a barcode label 61a only on the first-type sample container 61 and reading a sample number via a barcode reader from a barcode printed on the barcode label 61a, the present invention is not limited to this configuration. For example, barcode labels may be adhered to the first-type sample container 61 and the second-type sample container 62, so that the respective sample numbers can be read by the barcode reader from the barcode printed on the barcode label. The PPP sample at holding position 1 and the PRP sample at holding position 5 can be specified as collected from the same patient by comparing the read sample numbers.

Although the above embodiment is described in terms of the PPP sample measurement protocol and the PRP sample measurement protocol being different in the PPP sample measurement operation and the PRP sample measurement operation, the present invention is not limited to this configuration inasmuch as the PPP sample measurement protocol and the PRP sample measurement protocol also may be the same. For example, the PPP sample measurement protocol may be identical to the measurement protocol of the PRP sample in the embodiment described above. That is, the PPP sample may be heated for a predetermined time after the PPP sample is dispensed to a cuvette, then a platelet aggregation inducing agent identical to that used to measure the PRP sample may be dispensed to the cuvette, which is then irradiated by light to detect the light absorption.

Although the measurement items for platelet aggregation, e.g. "PPP" and "ADP", are automatically selected and measured when the user manually sets the operation mode in the above embodiment, the present invention is not limited to this configuration. Each measurement item for platelet aggregation also may be set individually.

Although the measurement unit 2 and the information processing unit 3 are provided separately in the sample analyzer 1 of the above embodiment, the present invention is not limited to this configuration. A sample analyzer also may be provided functions corresponding to the measurement unit and functions corresponding to the information processing unit within a single housing.

Although the above embodiment is described in terms of a sample analyzer for measuring PPP samples and PRP samples, the present invention is not limited to this configuration inasmuch as the invention is also applicable to sample analyzers for measuring a sample and a diluted sample, or sample analyzers for measuring a sample obtained by culturing the bacteria in a sample in a different medium.

What is claimed is:

1. A sample analyzer comprising:
    a transporting part configured to transport a sample rack configured to hold a first sample and a second sample;
    a measuring part configured to perform a first measurement on the first sample and a second measurement on the second sample; and
    a controller;
    wherein the controller is configured to perform an analysis of a blood platelet aggregation that requires at least a first measurement result and a second measurement result derived respectively from the first measurement of the first sample, preprocessed according to a platelet rich plasma (PRP) protocol, and the second measurement of the second sample, preprocessed according to a platelet poor plasma (PPP) protocol, respectively, the first sample and the second obtained from a same subject,
    if a measurement of the blood platelet aggregation is requested and the first sample and the second sample are transported to the measuring part, the controller controls the measuring part to perform the first measurement on the first sample and the second measurement on the second sample to derive the first and second measurement results and the controller processes the first and second measurement results to generate an analysis result of the blood platelet aggregation, and
    the controller is further configured to identify the location of the second sample according to the location of the first sample.

2. The sample analyzer of claim 1, wherein the controller is further configured to recognize the first sample and the second sample as a pair of samples used to analyze the blood platelet aggregation when a positional relationship of the first sample and the second sample held in a same or different sample racks satisfies a predetermined rule.

3. The sample analyzer of claim 2, wherein the controller is further configured to recognize the pair of samples on the same sample rack according to a predetermined positional relationship of the pair of samples.

4. The sample analyzer of claim 3, wherein the controller is further configured to recognize the pair of samples according to adjacent holding positions, of the first sample and the second sample, on the same sample rack.

5. The sample analyzer of claim 2, wherein the controller is further configured to recognize the first sample and the second sample according to a predetermined first holding position, of the first sample on the same sample rack, and a predetermined second holding position, of the second sample on the same sample rack.

6. The sample analyzer of claim 2, wherein the controller is further configured to recognize a sample number of the first sample according to a barcode attached to a container holding the first sample and to apply the sample number to the second sample which is held by a container without a barcode.

7. The sample analyzer of claim 1 further comprising a reading part configured to read an identification information attached to a sample container holding a sample;
    wherein the controller is further configured to recognize the sample within the sample container as designated for analysis of the blood platelet aggregation based on the identification information read from the sample container, and to recognize the sample within the sample container as the first sample used to analyze the blood platelet aggregation.

8. The sample analyzer of claim 7, wherein the controller is further configured to recognize a sample within a sample container held in a predefined holding position of the sample rack as the second sample paired with the first sample according to a predetermined rule.

9. The sample analyzer of claim 1, wherein the controller is further configured to control the measuring part to perform a first operation for measuring the first sample and to perform a second operation, which is different from the first operation, for measuring the second sample.

10. The sample analyzer of claim 9, wherein the measuring part comprises:
    a sample dispensing part configured to dispense a sample held in the sample rack to a reaction container;
    a reagent dispensing part configured to dispense a reagent from a reagent container to the reaction container; and
    a detecting part configured to detect a characteristic information of a reaction substance in the reaction container.

11. The sample analyzer of claim 10, wherein the first operation includes dispensing the first sample to the reaction container with the sample dispensing part, and detecting a first characteristic information of the first sample in the reaction container with the detecting part without dispensing the reagent to the reaction container;
    the second operation includes dispensing the second sample to the reaction container with the sample dispensing part, dispensing reagent from the reagent container to the reaction container with the reagent dispensing part, and detecting a second characteristic information of a mixture of the reagent and the second sample in the reaction container with the detecting part; and
    wherein the controller is further configured to generate the analysis result for the blood platelet aggregation based on the first characteristic information obtained by the first measurement operation and the second characteristic information obtained by the second measurement operation.

12. The sample analyzer of claim 11 further comprising a display section,
    wherein the controller is further configured to control the display section to display a screen showing the analysis results of the blood platelet aggregation, and
    the screen includes the first characteristic information and the second characteristic information.

13. The sample analyzer of claim 10, wherein the reagent is a blood platelet aggregation inducing agent.

14. The sample analyzer of claim 13, further comprising a display section,
    wherein the measuring part is further configured to analyze blood coagulation items indicating an amount or a degree of activity of a specific substance of blood coagulation or fibrinolytic function;

the controller is further configured to control the display section to display an analysis result of the blood coagulation item and the analysis result of the blood platelet aggregation on a same screen when measurements have been performed for items related to blood coagulation and blood platelet aggregation of at least two samples collected from a same subject.

15. The sample analyzer of claim 1, wherein the PRP preprocessing of the first sample comprises a first centrifugation condition and the PPP preprocessing of the second sample comprises a second centrifugation condition, different than the first centrifugation condition.

16. The sample analyzer of claim 1, wherein
the first sample and the second sample are derived from a whole blood sample obtained from a same subject,
the first sample is platelet rich plasma sample obtained by collecting a supernatant of the whole blood sample subjected to a weak centrifugation, and
the second sample is platelet poor plasma sample, obtained by collecting a supernatant of a remaining sample from which the first sample is collected, subjected to strong centrifugation, stronger than the weak centrifugation.

17. The sample analyzer of claim 1, wherein the controller is further configured to identify that the location of the second sample is at a sample rack other than a sample rack at which the first sample is located.

18. A sample analyzer comprising:
a transporting part configured to transport a sample rack configured to hold a first sample and a second sample;
a reading part configured to read identification information of the first sample and the second sample;
a measuring part configured to perform a first measurement of the first sample and a second measurement of the second sample; and
a controller configured to:
  specify an analysis of blood platelet aggregation with respect to the first sample according the identification information;
  designate the second sample, held in a same sample rack as the first sample or different sample rack than the first sample, as paired with the first sample according to a predetermined rule when the specified analysis of blood platelet aggregation is predetermined to use the first sample, preprocessed according to a platelet rich plasma (PRP) preprocessing protocol, and the second sample, preprocessed according to a platelet poor plasma (PPP) preprocessing protocol;
  cause the measuring part to perform the first measurement of the first sample and the second measurement of the second sample; and
  generate an analysis result of the blood platelet aggregation by processing respective measurement results of the first sample and the second sample, wherein
the controller is further configured to identify the location of the second sample according to the location of the first sample.

19. The sample analyzer of claim 18, wherein the controller is further configured to determine a position of the second sample from a position of the first sample on a same or a different sample rack.

20. The sample analyzer of claim 18, wherein the controller is further configured to control the measuring part to perform a first measurement, measuring the first sample, according to a PRP protocol and a second measurement, measuring the second sample, according to a PPP protocol that differs from the PRP protocol.

21. The sample analyzer of claim 20, wherein the controller is further configured to control the measuring part to perform the first measurement using a reagent, and to control the measuring part to perform the second measurement without using the reagent.

22. A sample analyzing method comprising:
transporting a sample rack holding a plurality of samples including both a first sample and a second sample each collected from a same subject and respectively subjected to a platelet rich plasma (PRP) preprocessing and platelet poor plasma (PPP) preprocessing, different than the PRP preprocessing;
identifying the first sample and the second sample from among the plurality of samples held in the sample rack;
measuring the identified first sample and second sample;
processing a first measurement result of measuring the first sample and a second measurement result of measuring the second sample to obtain an analysis result for a blood platelet aggregation; and
displaying the analysis result of the blood platelet aggregation, wherein
a location of the second sample is determined according to a location of the first sample.

23. A sample analyzer comprising:
a transporting part configured to transport a sample rack configured to hold a first sample and a second sample;
a measuring part configured to perform a first measurement on the first sample and a second measurement on the second sample; and
a controller;
wherein the controller is configured to perform an analysis of a blood platelet aggregation that requires at least a first measurement result and a second measurement result derived respectively from the first measurement of the first sample, preprocessed according to a platelet poor plasma (PPP) protocol, and the second measurement of the second sample, preprocessed according to a platelet rich plasma (PRP) protocol, respectively, the first sample and the second obtained from a same subject,
if a measurement of the blood platelet aggregation is requested and the first sample and the second sample are transported to the measuring part, the controller controls the measuring part to perform the first measurement on the first sample and the second measurement on the second sample to derive the first and second measurement results and the controller processes the first and second measurement results to generate an analysis result of the blood platelet aggregation, and
the controller is further configured to identify the location of the second sample according to the location of the first sample.

24. A sample analyzer comprising:
a transporting part configured to transport a sample rack configured to hold a first sample and a second sample;
a reading part configured to read identification information of the first sample and the second sample;
a measuring part configured to perform a first measurement of the first sample and a second measurement of the second sample; and
a controller configured to:
  specify an analysis of blood platelet aggregation with respect to the first sample according the identification information;
  designate the second sample, held in a same sample rack as the first sample or different sample rack than the first sample, as paired with the first sample according to a predetermined rule when the specified analysis of blood platelet aggregation is predetermined to use the first sample, preprocessed according to a platelet poor plasma (PPP) preprocessing protocol, and the second sample, preprocessed according to a platelet rich plasma (PRP) preprocessing protocol;

cause the measuring part to perform the first measurement of the first sample and the second measurement of the second sample; and generate an analysis result of the blood platelet aggregation by processing respective measurement results of the first sample and the second sample, wherein the controller is further configured to identify the location of the second sample according to the location of the first sample.

25. A sample analyzing method comprising:

transporting a sample rack holding a plurality of samples including both a first sample and a second sample each collected from a same subject and respectively subjected to a platelet poor plasma (PPP) preprocessing and platelet rich plasma (PRP) preprocessing, different than the PPP preprocessing;

identifying the first sample and the second sample from among the plurality of samples held in the sample rack;

measuring the identified first sample and second sample;

processing a first measurement result of measuring the first sample and a second measurement result of measuring the second sample to obtain an analysis result for a blood platelet aggregation;

displaying the analysis result of the blood platelet aggregation, and determining a location of the second sample is determined according to a location of the first sample.

* * * * *